(12) United States Patent
Tao

(10) Patent No.: US 8,927,707 B2
(45) Date of Patent: Jan. 6, 2015

(54) PURIFICATION METHOD OF AZTREONAM

(75) Inventor: Linggang Tao, Wuyi County (CN)

(73) Assignee: Hainan Lingkang Pharmaceutical Co., Ltd., Hainan (CN)

( * ) Notice: Subject to any disclaimer, the term of this patent is extended or adjusted under 35 U.S.C. 154(b) by 0 days.

(21) Appl. No.: 13/885,618

(22) PCT Filed: Mar. 17, 2011

(86) PCT No.: PCT/CN2011/000434
§ 371 (c)(1),
(2), (4) Date: May 15, 2013

(87) PCT Pub. No.: WO2012/100382
PCT Pub. Date: Aug. 2, 2012

(65) Prior Publication Data
US 2013/0296549 A1    Nov. 7, 2013

(30) Foreign Application Priority Data

Jan. 28, 2011 (CN) .......................... 2011 1 0031754

(51) Int. Cl.
*C07D 417/12* (2006.01)
*C07D 501/36* (2006.01)

(52) U.S. Cl.
CPC ............ *C07D 417/12* (2013.01); *C07D 501/36* (2013.01)
USPC ....................................... 540/355

(58) Field of Classification Search
CPC ................................. C07D 205/095
USPC .................................................. 540/355, 356
See application file for complete search history.

(56) References Cited

U.S. PATENT DOCUMENTS 4,752,469 A    6/1988    Sykes

FOREIGN PATENT DOCUMENTS

CN      101412715 A     4/2009
WO    WO/2006/122253 A1   11/2006

*Primary Examiner* — Golam M M Shameem
*Assistant Examiner* — Laura Daniel
(74) *Attorney, Agent, or Firm* — CBM Patent Consulting, LLC

(57) ABSTRACT

It discloses a process for refining Aztreonam, comprising the steps of 1) treating Aztreonam material with an alkali metal alkoxylate or an alkali earth metal alkoxylate under heating in the presence of a suitable solvent or a mixture of solvents, followed by adjusting the pH value with a suitable acid and cooling down to precipitate Aztreonam, which provides a primary purified Aztreonam; 2) adsorbing Aztreonam with strongly basic ion exchange resin, followed by eluting the resin and collecting the eluate, to provide a secondary purified Aztreonam after concentration under reduced pressure; 3) adjusting the pH value with a suitable acid to allow crystallization, followed by centrifuging and washing the resultant crystals, to provide a tertiary purified Aztreonam after drying. The refined Aztreonam product has a purity of no less than 99.2%, mostly no less than 99.5%, with little residue on ignition and significantly low content of heavy metals.

16 Claims, No Drawings

PURIFICATION METHOD OF AZTREONAM

FIELD OF THE INVENTION

The invention relates to medical technology, in particular, to a process for refining Aztreonam.

PRIOR ART

Aztreonam is a monobactam antibiotic, having the chemical name [2S-[2α,3β(Z)]]-2-[[[1-(2-amino-4-thiazolyl)-2-[(2-methyl-4-oxo-1-sulfo-3-azetidinyl)amino]-2-oxoethylene]amino]oxo]-2-methylpropionic acid, and a formula of $C_{13}H_{17}N_5O_8S_2$. It has a molar weight of 435.44 and the following structure:

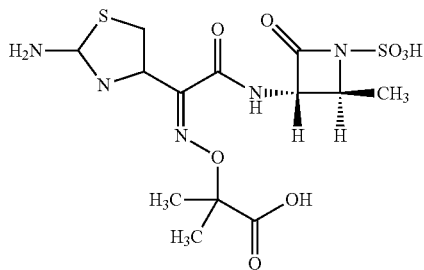 [SMILES: C[C@H]1[C@H](NC(=O)/C(=N\OC(C)(C)C(=O)O)C2CSC(N)N2)C(=O)N1S(=O)(=O)O]

Aztreonam, which is developed by Squibb Company (US), is an atypical β-lactam antibiotic which can be artificially synthesized. It entered the market in Italy in 1984. Aztreonam shows high antimicrobial activities against most of aerobic gram-negative bacteria, including *Escherichia coli, Bacillus pneumoniae* and *Klebsiella oxytoca* of *Klebsiella pneumoniae* genus, *Bacillus aerogenes, Bacillus cloacae, Proteus, Serratia, citrobacter, Shigella* and other Enterobacteriaceae, and *Hemophilus influenzae, Neisseria gonorrhoeae, Neisseria meningitidis*, etc., and also shows a good antibacterial activity against *P. aeruginosa*. It is clinically useful mainly for the treatment of various infections induced by sensitive aerobic gram-negative bacteria, such as urinary tract infection, lower respiratory tract infections, sepsis, intra-abdominal infections, gynecological infections, post-surgical wound and burns, ulcers and other infections relating to skin and soft tissues.

A number of references of patents and journals have disclosed Aztreonam and its crystalline forms and processes for preparing the same and for converting into crystalline forms.

U.S. Pat. No. 4,775,670 A discloses a process for preparing Aztreonam, wherein 2-(2-amino-4-thiazolyl)-2-(1-diphenylmethoxycarbonyl-1-methyl ethyloxy)imino acetic acid hydrochloride and (2S-trans)-3-amino-2-methyl-4-oxo-1-azetidinyl sulfonic acid undergo dehydrolysis in the presence of dicyclohexylcarbodiimide, then diphenylmethyl group is deprotected with trifluoroacetic acid and anisole, thus producing Aztreonam. In this process, the deprotection is realized through the reaction between acylated products and trifluoroacetic acid in the presence of anisole in an anhydrous condition. However, the agents used here are toxic and expensive.

As reported in CN Patent Application 1681812 A, Aztreonam can be prepared by reacting inorganic acid (hydrochloric acid, sulfuric acid, trifluoroacetic acid) with t-butyl aztreonam to remove t-butyl protection. A problem of the above process lies in that trifluoroacetic acid is expensive and unable to be recovered. Besides, the utilization of sulfuric acid causes the yield relatively low and produces ring-up products which can not be recycled as well and are dangerous to the environment.

U.S. Pat. No. 5,254,681 A discloses a process for preparing Aztreonam, comprising acylating azetidine with 2-(2-amino-4-thiazolyl)-2-(Z)-(alkoxylimino)acetic acid in the presence of 1-hydroxyl-benzotriazole and dicyclohexylcarbodiimide. However, the agents used in the process are toxic, expensive, and are also difficult to handle.

Although the processes mentioned above can produce Aztreonam effectively, the inevitable problem is that the purity of the targeted product is unsatisfactory. Such processes provided for treating or purifying products are conventional in organic synthesis, and themselves are almost unable to produce a purity of 95% or more. Therefore, some companies have developed several purifying and refining processes for Aztreonam.

SICOR Inc. (US) discloses a process for preparing and purifying Aztreonam in the International Application WO2006/122253, wherein a reactant containing t-butyl Aztreonam (one of the precursors containing Aztreonam) is adjusted with an acid, i.e. with HCl to a pH of about 1.5 and then diluted with water so as to increase the purity of the desired product.

Aurobindo Pharma Ltd. (India) discloses a process for preparing Aztreonam with enhanced purity, which comprises dissolving the α-form of Aztreonam in absolute ethanol at a temperature of −10~15° C. and warming the solution to 50~55° C. after sterile filtration to crystallize anhydrous β-form of Aztreonam, thus realizing the refinement. However, due to four crystal forms of Aztreonam such as α-, β-, γ- and δ-forms, rigid requirement of the raw materials is necessary for this process, and moreover only single product can be obtained. In addition, the inherent impurities can not be removed simply through dissolving, warming and crystallizing, and the peritectic is also inevitable.

Chinese Patent Application CN101412715 A (granted as CN101412715 B) discloses a process for refining Aztreonam compound, wherein crude Aztreonam is treated with a basic solution to adjust the pH value, and purified through Hp-20 resin; the obtained eluate is collected and concentrated under reduced pressure, and then treated with an acidic solution to adjust the pH value and precipitate the solid which undergoes centrifugation, washing, and drying to produce a refined product of Aztreonam. Although the process can improve the purity of Aztreonam, such a neutral resin as Hp-20 resin does not demonstrate a satisfactory purification efficiency for Aztreonam since the latter has a high polarity. Moreover, additional negative ion impurities may be introduced during adjusting the pH value, thereby increasing the difficulty in isolation.

DETAILED DESCRIPTION OF THE INVENTION

The invention provides a process for refining Aztreonam compound, which overcomes the above defects existing in the prior art, especially the low purity of Aztreonam prepared by the prior art.

The Aztreonam useful in the present refining process can be crude Aztreonam obtained from any known process in the art for preparing Aztreonam or any commercially available Aztreonam drug substance, hereinafter all referred to as Aztreonam material used according to the present invention.

After intensive study, the inventor surprisingly found that the purity of Aztreonam material can be substantially improved by a refining process which comprises the steps of:

1) treating Aztreonam material with an alkali metal alkoxylate or an alkali earth metal alkoxylate under heating in the presence of a suitable solvent or a mixture of solvents, followed by adjusting the pH value with a suitable acid and cooling down to precipitate Aztreonam, thereby providing a primary purified Aztreonam;

2) adsorbing Aztreonam with strongly basic ion exchange resin, followed by eluting the resin and collecting the eluate, to provide a secondary purified Aztreonam after concentration under reduced pressure; and 3) adjusting the pH value with a suitable acid to allow crystallization, followed by centrifuging and washing the resultant crystals, to provide a tertiary purified Aztreonam after drying.

The invention is further illustrated as follows.

Step 1)

Aztreonam material is treated with an alkali metal alkoxylate or an alkali earth metal alkoxylate under heating in the presence of a suitable solvent or a mixture of solvents, followed by adjusting the pH value with a suitable acid and cooling down to precipitate Aztreonam, thereby providing a primary purified Aztreonam.

Any solvent or mixture of solvents that can dissolve or suspend Aztreonam may be used.

The solvent is selected from lower alcohols, non-alcoholic polar solvents, and mixture thereof that can homogenize the reaction mixture. The lower alcohols can be used as solvent, including, but not limited to, a primary alcohol, a secondary alcohol or a tertiary alcohol with 1 to 6 carbon atoms, preferably methanol, ethanol, propanol or any mixture thereof. The non-alcoholic polar solvent is selected from a group consisting of N,N-dimethylformamide, dimethylsulfoxide, tetrahydrofuran, 1,4-dioxane and/or N-methyl morpholine. A mixture of two or more lower alcohols and/or non-alcoholic polar solvents can also be used.

In a preferred embodiment, the solvent used has the same moiety as the anion moiety of the alkali metal alkoxylate or the alkali earth metal alkoxylate, such as alcoholic solvent, e.g. methanol, ethanol, propanol or butanol.

In general, any alkali metal or alkali earth metal alkoxylate (i.e. alkoxide) can be used, with alkali metal alkoxylate preferable and alkoxylate of potassium or sodium more preferable, such as sodium methoxide, sodium ethoxide, and potassium methoxide or potassium ethoxide.

Typically, alkali metal or alkali earth metal alkoxylate is firstly dissolved in an alcoholic solvent, preferably a solvent has the same anion moiety thereof. For example, sodium methoxide or potassium methoxide is dissolved in methanol, and sodium ethoxide or potassium ethoxide is dissolved in ethanol.

The treatment of Aztreonam with alkali metal alkoxylate or alkali earth metal alkoxylate can be carried out at a temperature of 30~100° C., preferably at a temperature of 40~80° C. The treatment is more preferably carried out at a temperature of 50~70° C. to allow a sufficient hydrolysis.

After the above treatment, the pH value is adjusted with a suitable acid. The Aztreonam precipitates as the temperature drops.

According to the invention, inorganic acids can be used in the step, such as hydrochloric acid, sulfuric acid and phosphoric acid. Organic acid, such as organic carboxylic acid or organic sulfonic acid can also be used. The acid used herein is preferably selected from a group consisting of benzenesulfonic acid, p-fluorobenzenesulfonic acid, p-trifluoromethyl benzenesulfonic acid, naphthalenesulfonic acid, formic acid, acetic acid, propanoic acid and so on, with benzenesulfonic acid, p-fluorobenzenesulfonic acid, p-trifluoromethyl benzenesulfonic acid and formic acid more preferable.

According to the present invention, the pH value in this step is adjusted to a range between 1.0 and 3.0, preferably between 1.5 and 2.5.

Without being bound to any theory, treating Aztreonam with an alkali metal alkoxide or an alkali earth metal alkoxide in the step 1) of the invention can achieve a purification effect probably due to the following reasons:

In many processes for preparing Aztreonam, the final step is to remove carboxyl-protecting groups, such as ester group which is a common protecting group for carboxyl. This will inevitably introduce a trace amount of ester impurities into crude Aztreonam. The presence of basic substances such as alkali metal alkoxylate or alkaline earth metal alkoxylate contributes to hydrolyzing the residual esters into Aztreonam, which not only reduces the impurities effectively, but also increases favorably the yield of targeted product. In addition, some impurities can be dissolved in the alcoholic solvents containing alkali metal alkoxylate or alkaline earth metal alkoxylate, and thus be separated from Aztreonam.

Step 2)

It should be noticed that the process for refining Aztreonam as disclosed in CN 101412715 A is carried out in two steps: crude Aztreonam is treated with a basic solution to adjust the pH value, and then purified through Hp-20 resin to collect the eluate. In addition to the complicated operations, additional negative ions can be introduced by adjusting the pH value. Such a neutral resin as Hp-20 resin does not exhibit a satisfactory purification efficiency for Aztreonam with a high polarity. The use of strongly basic ion exchange resin can efficiently overcome these drawbacks.

In step 2), Aztreonam is adsorbed onto the strongly basic ion exchange resin and then eluted, after which the eluate is collected and concentrated under reduce pressure to give a secondary purified Aztreonam.

In general, the ion exchange resin which utilizes quaternary ammonium as the exchanging group is known as strongly basic ion exchange resin, which shows alkaline by the dissociation of hydroxide ions. Common strongly basic ion exchange resin is obtained from chloromethylating and tertiary-aminating the styrene-divinylbenzene copolymer spherical particles. Type I strongly basic anion resin is obtained from the amination with trimethylamine; type II strongly base anion resin is obtained from amination with dimethyl ethanolamine.

Generally, Aztreonam material contains solvents, various raw materials and intermediate products, which are introduced during the preparation, and also contains moisture due to hygroscopicity, bacterial endotoxin, various inorganic substances and heavy metals, and so on. Theses substances are present in the form of impurities which affect the purity of Aztreonam material. The strongly basic resins used in the present invention have the general functions as ion exchange resins do. When the strongly basic resin is contacted with a solution containing Aztreonam, in addition to playing a role of ion exchange, it can adsorb non-electrolyte substances from the solution and thus can adsorb the residual impurities. In addition, the resin itself has a bleaching effect to remove any impurity that can endow others a color, and such effect is better than that of activated carbon.

The strongly basic resin used in the invention is itself a macroporous ion exchange resin, and has a physical pore structure similar to that of activated carbon and zeolite. The diameter of larger pores is much greater than the intermolecular distance, and the pore sizes are also in the order of dozens of angstroms to ten thousands of angstroms. Although macropores do not constitute the polymer gel morphology of the resin, its presence results in the polymer gel with a two-phase structure, i.e. macropores and polymer gel matrix, wherein the macropores take a certain space in the resin sphere. There are also gel pores in the gel matrix. The above structural characteristics constitute the physical basis of the functions of macroporous ion exchange resin.

The invention can use common macroporous strongly basic ion exchange resins, such as the polystyrene type I strongly basic anion resins of Amberlite IRA-900 and IRA-904, Type II strongly basic anion resin of IRA-911, macroporous strongly basic styrenic anion exchange resin of D201, strongly basic anion macroporous resin of D-235, strongly basic anion exchange resin of 201X 7, and so on. All these strongly basic anion resins are commercially available. Of course, macroporous strongly basic ion exchange resins with other trade names can also be used.

According to the present invention, Aztreonam-containing solution can pass through the strongly basic anion resin in a continuous or non-continuous process. Specifically, the useful processes include batch process, fixed bed process and continuous process.

The batch process is carried out in a reaction tank. The exchange solution flows into the tank from the bottom, and the ion exchange equilibrium is accelerated by continuously introducing a gas to fluidize the resin or by stirring. The exchange process is stopped after the equilibrium is achieved, and then the solution is released from the bottom.

In a fixed bed process, the ion exchange resin is packed into an exchange column to form a resin bed, and then a solution is introduced for processing. During a fixed-bed operation, the solution typically flows from top to bottom in a manner as forward flow, or from bottom to top in a countercurrent regeneration manner, i.e. flowing in the opposite direction against the exchange solution. A convection-type counter-current manner can also be useful.

In general, Aztreonam has a pH value between 2.2 and 2.8 due to its high polarity per se and the carboxyl group and the sulfonic group it carries. The pH value of Aztreonam can be increased typically to a pH of 5.0~6.0, after passing through strongly basic ion exchange resin.

When an equilibrium is reached, the adsorbed Aztreonam is eluted off in the form of alkali metal salt after being eluted with a solution of alkali metal hydroxide or other suitable alkaline substances (called resin regeneration), preferably with an aqueous or alcoholic solution of alkali metal hydroxide. A mixed solution of water and alcohols can also be useful. The eluate is collected, and concentrated under a reduced pressure.

Step 3)

In this step, the pH is adjusted with a suitable acid to precipitate the crystals, which is centrifuged, washed and dried to give a tertiary purified Aztreonam.

According to the invention, organic acids, in particular, organic carboxylic acids or organic sulphonic acids, can be used in this step. The acid used herein is preferably selected from a group consisting of benzenesulfonic acid, p-fluorobenzenesulfonic acid, p-trifluoromethyl benzenesulfonic acid, naphthalenesulfonic acid, formic acid, acetic acid, propanoic acid, tartaric acid, citric acid, malonic acid and so on, more preferably benzenesulfonic acid, p-fluorobenzenesulfonic acid, p-trifluoromethyl benzenesulfonic acid, naphthalenesulfonic acid and formic acid, most preferably benzenesulfonic acid, p-fluorobenzenesulfonic acid, p-trifluoromethyl benzenesulfonic acid and formic acid.

According to the invention, the pH value in this step is adjusted to 1.0~4.0, preferably 1.5~3.0, most preferably 1.8~2.5.

Without being bound to any theory, the reason for the purity of Aztreonam being increased after adjusting with an acid in the present step 3) is as follows:

As described in CN101412715A, the pH value of the mother liquor eluted from Hp-20 resin is adjusted with such inorganic acid as hydrochloric acid, sulfuric acid or nitric acid to allow crystallization. However, these inorganic strong acids used generally lead to partial hydrolysis of amide bond and destruction of thiazole ring. In contrast, the step 3) of the invention utilizes acids with moderate acidity and having the same anion as the carboxyl moiety or sulfonic moiety of Aztreonam, which is advantageous for a smooth crystallization of Aztreonam without the inclusion of additional anions.

EMBODIMENTS OF THE INVENTION

The invention provides a process for refining Aztreonam, characterized in comprising the steps of:

1) treating Aztreonam material with alkali metal alkoxylate dissolved in an alcoholic solvent at a temperature between 30° C. and 100° C., preferably between 40° C. and 80° C., in the presence of a lower alcohol or a non-alcoholic polar solvent or mixture thereof, at a preferable treating temperature of 50° C.~70° C., followed by adjusting the pH value with a suitable acid and cooling down to precipitate Aztreonam, to provide a primary purified Aztreonam;

2) adsorbing Aztreonam with strongly basic ion exchange macroporous resin, followed by eluting the resin with a solution of alkali metal hydroxide and collecting the eluate and then concentrating under reduced pressure;

3): adjusting the pH value to 1.0 to 4.0 with an organic carboxylic acid or organic sulfonic acid to allow crystallization, followed by centrifuging and washing the resultant crystals, to provide a refined Aztreonam after drying.

In an embodiment of the invention, the lower alcohol solvent comprises a primary alcohol, a secondary alcohol or a tertiary alcohol with 1 to 6 carbon atoms, preferably methanol, ethanol, propanol or any mixture thereof.

In an embodiment of the invention, the non-alcoholic polar solvent in step 1) is selected from N,N-dimethylforfamide, dimethylsulfoxide, tetrahydrofuran, 1,4-dioxane and/or N-methyl morpholine.

In an embodiment of the invention, the alkali metal alkoxylate is preferably an alkoxylate of sodium or potassium, such as sodium methoxide, sodium ethoxide, potassium methoxide or potassium ethoxide; wherein the sodium methoxide or potassium methoxide is preferably dissolved in methanol, and the sodium ethoxide or potassium ethoxide is preferably dissolved in ethanol.

In an embodiment of the invention, the pH value in step 1) is adjusted with hydrochloric acid, sulfuric acid, or phosphoric acid, or with benzenesulfonic acid, p-fluorobenzenesulfonic acid, p-trifluoromethyl benzenesulfonic acid, naphthalenesulfonic acid, formic acid, acetic acid or propanoic acid. The pH value in this step is preferably adjusted to 1.5~2.5.

In an embodiment of the invention, the pH value of Aztreonam in step 2) is adjusted to 5.0~6.0. The aqueous or alcoholic solution of alkali metal hydroxide is used as the eluent.

In an embodiment of the invention, the acid used in step 3) is selected from a group consisting of benzenesulfonic acid, p-fluorobenzenesulfonic acid, p-trifluoromethyl benzenesulfonic acid, naphthalenesulfonic acid, formic acid, acetic acid, propanoic acid, tartaric acid, citric acid and malonic acid, wherein benzenesulfonic acid, p-fluorobenzenesulfonic acid, p-trifluoromethyl benzenesulfonic acid and formic acid are preferable. The pH value of this step is adjusted to pH 1.5~3.0, preferable 1.8~2.5.

The refined Aztreonam obtained from the above embodiments shows that impurity stain is controlled to no more than 0.8%, mostly no more than 0.5%, as TLC shows (developing solvent: acetonitrile:water=4:1). Therefore, the refined Aztreonam obtained according to the invention has a purity of not less than 99.2%, mostly no less than 99.5%.

The refined Aztreonam according to the invention contains little residue on ignition after burning, and very low content of heavy metals.

Since the powder flowability, specific dissolution rate, solid stability of Aztreonam and the operatablitity of the process play important roles in the activity of Aztreonam and the preparations thereof, Aztreonam with substantially increased purity brings about a significant improvement in the dissolution rate, the formulatability and the stability.

Therefore, the refined Aztreonam according to the invention is highly suitable for formulating an antimicrobial pharmaceutical composition for the treatment of various infections due to sensitive aerobic gram-negative bacteria, wherein the pharmaceutical composition comprises the refined Aztreonam according to the invention and pharmaceutically acceptable excipients. Preferably, the pharmaceutical composition can be a freeze-dried powder.

The invention also provides a use of the pharmaceutical composition in the preparation of a antimicrobial medicine for the treatment of various infections due to sensitive aerobic gram-negative bacteria; the above infections preferably includes urinary tract infections, lower respiratory tract infection, sepsis, intra-abdominal infections, gynecological infections, surgical wound and burns, ulcers and other infections relating to skin and soft tissues.

The present invention has fundamentally enhanced the lower purity of the current Aztreonam material, solved the problem existing in crude Aztreonam material and Aztreonam drug substances, reduced a series of clinical adverse reactions due to the presence of excessive impurities. In addition, the present invention yields Aztreonam in a high ratio and a high purity of no less than 99%, mostly no less than 99.2%, with a overall yield of no less than 92%. The present invention also has advantages of convenience, easy to control and industrialization.

The following examples are intended to further explain or illustrate the invention, and the examples provided should not be understood as limiting the scope of the invention.

D201 macroporous strongly basic styrene anion exchange resin available from Resin Factory of Wandong, Anhui, or Amberlite®IRA-900 anion exchange resin was used in the examples.

I. The Measurement of the Purity for Aztreonam

Method I:

Thin layer chromatography (TLC) was performed on Aztreonam samples, using a developer of acetonitrile:water=4:1. The spots were examined corresponding to amounts of impurity.

Method II:

Octadecylsilane chemically bonded silica was used as fillers in the chromatography conditions and system applicability test; methanol –0.05 mol/L sodium heptanesulfonate-phosphate buffer (6.8 g of potassium dihydrogen phosphate was dissolved and diluted by adding water to 1000 ml) (28:22:50) was used as mobile phase; the detection wavelength was 254 nm. The theoretical plate number should be no less than 1500 calculated based on the peak of Aztreonam. The ratio of the composition of the mobile phase can be adjusted, if necessary, to achieve a resolution between Aztreonam main peak and neighboring purity peak of no less than 3.0.

The specific operation is described as follows:

A suitable amount of Aztreonam sample is added with 1 ml of mobile phase to form a solution containing 1 mg Aztreonam per ml, which is used as a test solution; a precise amount of Aztreonam was added with 1 ml of mobile phase to form a solution containing 0.01 mg Aztreonam per ml, which is used as a control solution. The content is determined according to the following procedure: taking 20 μL of control solution which is injected into a liquid chromatograph, adjusting the sensitivity, so that the peak of main component has a height corresponding to 10%~15% of the full-scale peak height, then 20 μL of the test solution and control solution are taken and injected into the liquid chromatograph, respectively. The chromatogram is recorded until 2 times the retention time of the peak for main component. In the test solution of the chromatogram, the area of any single purity peak, such as significant impurities, should be not larger than the area of main peak from the control solution (1.0%), and the total area of impurity peaks should be not larger than 2 times the area of the main peak from the control solution (2.0%).

II. Measurement of Residue on Ignition:

1 g of Azetronam sample was taken and examined according to the regulations (Chinese Pharmacopoeia 2, Appendix VIII N, the 2000 edition). Considering that the residue will be used to measure the content of heavy metals in the following step, the ignition has a temperature of 500-600° C. Three samples were taken for each test to give an average. The residue is normally required as no more than 0.1%.

III. Measurement of the Content of Heavy Metals:

The samples, taken from the remaining of the residue on ignition test, were examined according the regulation (Chinese Pharmacopoeia 2, Appendix VIII H, Method II, the 2000 edition). 3 samples were measured for each time to give an average, which was compared to a reference made from 1.0 ml standard lead solution (10 ppm). The content of heavy metals was normally required as no more than 20 ppm.

Example 1

20 ml ethanol was added under stirring into 10 g of Azetronam with a purity of 95% according to U.S. Pat. No. 4,775,670 A. A 1 mol/L solution of sodium ethoxide in ethanol was added at 30° C. before heating slowly to 60° C., and then treating for 2 hs under stirring. The pH value was adjusted to 1.5 with hydrochloric acid, then cooling to room temperature to precipitate Azetronam. At this time, impurity stain was examined by TLC (developing solvent: acetonitrile:water=4:1) as 2.5%.

The solution containing Azetronam was loaded into a fixed bed filled with D201 macroporous strongly basic styrene-based anion exchange resin before the exchange proceeded until the pH value was adjusted to 5.2. Then an elution was performed using an aqueous solution of sodium hydroxide as the eluent to obtain an eluate which was collected and concentrated under reduced pressure. At this time, impurity stain was examined by TLC (developing solvent: acetonitrile:water=4:1) as 0.8%.

The pH value was adjusted with 0.5 mol/L p-fluorobenzenesulfonic acid to 1.2, then the solution was kept standing to start precipitating solids. No more solids precipitated 1 hour later. After centrifuged in a centrifuger and filtered, the obtained cake was washed with analytically pure ethanol, dried in vacuum at 30° C. for 6 hours to provide 9.5 g of refined Azetronam with a yield of 95%.

Impurity stain was examined by TLC (developing solvent: acetonitrile:water=4:1) as 0.3%. The purity was measured as 99.6% when using Method II. The averaged residual on ignition was 0.02%. The averaged content of heavy metals was 8 ppm.

Comparative Example 1

Crude Azetronam with a purity of 95%, prepared according to U.S. Pat. No. 4,775,670 A, was purified according to the refining process as described in Chinese patent CN101514200. 2 g of crude Azetronam was added to an anhydrous ethanol followed by heating, dissolving under stirring. Then the activated carbon was added for adsorption, and filtered out when still hot. The solution was cooled to precipitate solids which underwent filtering, washing with water and drying to give a white refined β-Azetronam. Impurity stain was examined by TLC (developing solvent: acetonitrile:water=4:1) as 3.5%. The averaged residual on ignition was 0.12%. The averaged content of heavy metals was 40 ppm.

Example 2

20 ml dimethyl sulfoxide was added under stirring into 10 g of Azetronam drug with a purity of 97%. A 1 mol/L solution of sodium methoxide in methanol was added at room temperature before heating slowly to 50° C., and then treating for 2.5 hs under stirring. The pH value was adjusted to 1.8 with p-fluorobenzenesulfonic acid, then cooling to room temperature to precipitate Azetronam. At this time, Impurity stain was examined by TLC (developing solvent: acetonitrile:water=4:1) as 1.5%.

The solution containing Azetronam was loaded into a fixed bed filled with D201 macroporous strongly basic styrene-based anion exchange resin before the exchange proceeded until the pH value was adjusted to 5.5. Then an elution was performed using a solution of sodium hydroxide in ethanol as the eluent to obtain an eluate which was collected and concentrated under reduced pressure. At this time, impurity stain was examined by TLC (developing solvent: acetonitrile:water=4:1) as 0.7%.

The pH value was adjusted with 0.5 mol/L formic acid to 1.5, then the solution was kept standing to start precipitating solids. No more solids precipitated 1.5 hs later. After centrifuged in a centrifuger and filtered, the obtained cake was washed with pure water, dried in vacuum at 30° C. for 6 hours to provide 9.6 g of refined Azetronam with a yield of 96%.

Impurity stain was examined by TLC (developing solvent: acetonitrile:water=4:1) as 0.35%. The purity was measured as 99.7% when using Method II. The averaged residual on ignition was 0.01%. The averaged content of heavy metals was 5 ppm.

Comparative Example 2

Azetronam drug with a purity of 97% was purified according to the refining process as described in CN 101412715 A. The crude Azetronam was added into a basic solution followed by adjusting the pH value. After purified with Hp-20 resin, the obtained eluate was collected and concentrated under reduced pressure. Then the pH value was adjusted with an acidic solution to precipitate solids which was centrifuged, washed and dried to provide a refined product of Azetronam. Impurity stain was examined by TLC (developing solvent: acetonitrile:water=4:1) as 1.8%.

Example 3

20 ml tetrahydronfuran was added under stirring into 10 g of crude Azetronam with a purity of 96% according to CN 1681812 A. A 1 mol/L solution of potassium ethoxide in ethanol was added at 40° C. before heating slowly to 65° C., and then treating for 1 h under stirring. The pH value was adjusted to 2.0 with formic acid, then cooling to room temperature to precipitate Azetronam. At this time, Impurity stain was examined by TLC (developing solvent: acetonitrile:water=4:1) as 2.0%.

The solution containing Azetronam was loaded into a reaction tank filled with Amberlite® IRA-900 anion exchange resin and the exchange was accelerated by introducing $CO_2$ until the pH value was adjusted to 5.8. Then an elution was performed using a solution of potassium hydroxide in ethanol as the eluent to obtain an eluate which was collected and concentrated under reduced pressure. At this time, Impurity stain was examined by TLC (developing solvent: acetonitrile:water=4:1) as 0.8%.

The pH value was adjusted with 0.8 mol/L aqueous benzenesulfonic acid to 1.5, then the solution was kept standing to start precipitating solids. No more solids precipitated 1 hour later. After centrifuged in a centrifuger and filtered, the obtained cake was washed with a mixture of ethanol/ethyl acetate, dried in vacuum at 30° C. for 6 hours to provide 9.6 g of refined Azetronam with a yield of 96%.

Impurity stain was examined by TLC (developing solvent: acetonitrile:water=4:1) as 0.5%. The purity was measured as 99.5% when using Method II. The averaged residual on ignition was 0.03%. The averaged content of heavy metals was 9 ppm.

Example 4

20 ml ethanol was added under stirring into 10 g of crude Azetronam drug with a purity of 98%. A 1 mol/L solution of potassium ethoxide in ethanol was added at room temperature before heating slowly to 60° C., and then treating for 1 h under stirring. The pH value was adjusted to 1.5 with benzenesulfonic acid, then cooling to room temperature to precipitate Azetronam. At this time, Impurity stain was examined by TLC (developing solvent: acetonitrile:water=4:1) as 1.3%.

The solution containing Azetronam was loaded into a fluidized bed filled with Amberlite® IRA-900 anion exchange resin before the exchange proceeded until the pH value was adjusted to 6.0. Then an elution was performed using a solution of potassium hydroxide in ethanol as the eluent to obtain an eluate which was collected and concentrated under reduced pressure. At this time, Impurity stain was examined by TLC (developing solvent: acetonitrile:water=4:1) as 0.6%.

The pH value was adjusted with a 0.5 mol/L aqueous acetic acid to 3.0, then the solution was kept standing to start precipitating solids. No more solids precipitated 2 hs later. After centrifuged in a centrifuger and filtered, the obtained cake was washed with analytically pure ethanol, and dried in vacuum at 30° C. for 6 hours to provide 9.7 g of refined Azetronam with a yield of 97%.

Impurity stain was examined by TLC (developing solvent: acetonitrile:water=4:1) as 0.2%. The purity was measured as 99.7% when using Method II. The averaged residual on ignition was 0.02%. The averaged content of heavy metals was 6 ppm.

The invention has been already illustrated according to the above examples. The foregoing examples are only intended to exemplify the invention. It will be appreciated that numerous modifications and embodiments may be devised by the skilled in the art without deviating the spirit and essence of the invention. Such modifications are also understood to fall within the scope of the invention.

What is claimed is:

1. A process for refining Aztreonam comprising the following steps:
   1) treating a crude Aztreonam with an alkali metal alkoxylate or an alkali earth metal alkoxylate with heat in a suitable solvent or a mixture of solvents, then adjusting pH with a suitable acid and cooling to precipitate Aztreonam which yields a primary purified Aztreonam;
   2) loading the primary purified Aztreonam into a strongly basic ion exchange resin, then eluting the resin and collecting eluate which is concentrated by a reduced pressure to yield a secondary purified Aztreonam; and
   3) adjusting pH value with a suitable acid to allow crystallization, then centrifuging, washing and drying the resultant crystals to yield a tertiary purified Aztreonam.

2. The process for refining Aztreonam according to claim 1, wherein said heat adjusts the temperature at a range between 30° C. and 100° C.

3. The process for refining Aztreonam according to claim 1, characterized in that, the alkali metal alkoxylate is an alkoxylate of potassium or sodium selecting from the group consisting of sodium methoxide, sodium ethoxide, potassium methoxide and potassium ethoxide; wherein the sodium methoxide or potassium methoxide is dissolved in methanol, and the sodium ethoxide or potassium ethoxide is dissolved in ethanol.

4. The process for refining Aztreonam according to claim 1, characterized in that, the pH value of Aztreonam in step 1) is adjusted to a range between 5.0 and 6.0; and an aqueous or alcoholic solution of an alkali metal hydroxide is used as eluent in step 2).

5. The process for refining Aztreonam according to claim 1, characterized in that, the acid used in step 3) is selected from a group consisting of benzenesulfonic acid, p-fluorobenzenesulfonic acid, p-trifluoromethyl benzenesulfonic acid, naphthalenesulfonic acid, formic acid, acetic acid, propanoic acid, tartaric acid, citric acid and malonic acid.

6. The process for refining Aztreonam according to claim 1, characterized in that, the acid used in step 3) is selected from a group consisting of benzenesulfonic acid, p-fluorobenzenesulfonic acid, p-trifluoromethyl benzenesulfonic acid or formic acid.

7. The process for refining Aztreonam according to claim 1, characterized in that, the pH value in step 3) is adjusted to a range between 1.0 and 4.0.

8. The process for refining Aztreonam, comprising the following steps:
   1) treating a crude Aztreonam with an alkali metal alkoxylate dissolved in an alcoholic solvent at a temperature between 30° C. and 100° C. in a lower alcohol or a non-alcoholic polar solvent or mixture thereof at a temperature between 50° C. and 70° C., followed by adjusting the pH with a suitable acid and cooling to precipitate Aztreonam which yields a primary purified Aztreonam;
   2) loading said primary purified Aztreonam onto a strongly basic ion exchange macroporous resin, followed by eluting the resin with a solution of an alkali metal hydroxide, collecting the eluate which is then concentrated by the reduced pressure; and
   3) adjusting the pH to a range between 1.0 and 4.0 with an organic carboxylic acid or organic sulfonic acid to allow crystallization, followed by centrifuging, washing and drying resultant crystals, which produces a refined Aztreonam.

9. The process for refining Aztreonam according to claim 8, wherein the lower alcohol is one or a mixture selected from a group consisting of a primary alcohol, a secondary alcohol and a tertiary alcohol with 1 to 6 carbon atoms.

10. The process for refining Aztreonam according to claim 8, wherein the lower alcohol is one or a mixture selected from a group consisting of methanol, ethanol and propanol.

11. The process for refining Aztreonam according to claim 8, characterized in that, the non-alcoholic polar solvent in step 1) is selected from a group consisting of N,N-dimethylformamide, dimethylsulfoxide, tetrahydrofuran, 1,4-dioxane and N-methyl morpholine.

12. The process for refining Aztreonam according to claim 8, characterized in that, the alkali metal alkoxylate is an alkoxylate of potassium or sodium selecting from the group consisting of sodium methoxide, sodium ethoxide, potassium methoxide and potassium ethoxide; wherein the sodium methoxide or potassium methoxide is dissolved in methanol, and the sodium ethoxide or potassium ethoxide is dissolved in ethanol.

13. The process for refining Aztreonam according to claim 8, characterized in that, the pH value of Aztreonam in step 1) is adjusted to a range between 5.0 and 6.0; and an aqueous or alcoholic solution of an alkali metal hydroxide is used as eluent in step 2).

14. The process for refining Aztreonam according to claim 8, characterized in that, the acid used in step 3) is selected from a group consisting of benzenesulfonic acid, p-fluorobenzenesulfonic acid, p-trifluoromethyl benzenesulfonic acid, naphthalenesulfonic acid, formic acid, acetic acid, propanoic acid, tartaric acid, citric acid and malonic acid.

15. The process for refining Aztreonam according to claim 8, characterized in that, the acid used in step 3) is selected from a group consisting of benzenesulfonic acid, p-fluorobenzenesulfonic acid, p-trifluoromethyl benzenesulfonic acid or formic acid.

16. The process for refining Aztreonam according to claim 8, characterized in that, the pH value in step 3) is adjusted to a range between 1.5 and 3.0.

\* \* \* \* \*